United States Patent [19]
Reis

[11] Patent Number: 6,077,940
[45] Date of Patent: Jun. 20, 2000

[54] FREE SOLUTION LIGAND INTERACTION MOLECULAR SEPARATION METHOD

[75] Inventor: Robert Van Reis, Redwood City, Calif.

[73] Assignee: Genentech, Inc., South San Francisco, Calif.

[21] Appl. No.: 08/998,413

[22] Filed: Dec. 24, 1997

[51] Int. Cl.[7] .............................. B01D 61/00; A23J 1/00; C07K 16/00
[52] U.S. Cl. ...................... 530/412; 530/417; 530/387.1; 436/828; 436/161; 210/656; 210/635
[58] Field of Search ..................................... 210/650, 652, 210/767, 512.1, 656, 635; 530/344, 387.1, 412, 417; 436/828, 161

[56] References Cited

U.S. PATENT DOCUMENTS

| | | | |
|---|---|---|---|
| 4,762,617 | 8/1988 | Stevens et al. | |
| 4,780,210 | 10/1988 | Hsia | 210/638 |
| 4,960,702 | 10/1990 | Rice et al. | 435/226 |
| 5,053,334 | 10/1991 | Arathoon et al. | 435/226 |
| 5,356,637 | 10/1994 | Loosen et al. | 426/7 |
| 5,490,937 | 2/1996 | van Reis | 210/637 |
| 5,759,404 | 6/1998 | Ericsson et al. | 210/638 |

FOREIGN PATENT DOCUMENTS

| | | |
|---|---|---|
| 104356 | 4/1984 | European Pat. Off. . |
| 87/04169 | 7/1987 | WIPO . |

OTHER PUBLICATIONS van Eijndhoven, R.H.C.M., et al., "Protein Fractionation Using Electrostatic Interactions in Membrane Filtration", *Biotechnology and Bioengineering*, vol. 48, pp:406–414 (1995).

Dong, X.Y., et al., "Multistage affinity cross–flow filtration: mathematical modelling and analysis", *Bioprocess Engineering*, vol. 15, pp. 99–104 (1996).

Flaschel, E., et al., "Ultrafiltration for the Separation of Biocatalysis", *Advances in Biochemical Engineering/Biotechnology*, vol. 26, pp. 123–140 (1983).

Ling, T.G.I., et al., "Membrane Filtration Affinity Purification (MFAP) of Dehydrogenases Using Cibacron Blue", *Biotechnology and Bioengineering*, vol. 24, pp. 1321–1325 (1989).

Nguyen, A.L., et al., "Synthesis and Applications of Water–Soluble Reactive Polymers for Purification and Immobilization of Biomolecules", *Biotechnology and Bioengineering*, vol. 34, pp. 1186–1190 (1989).

Janson, Jan–Christer, et al., "A Bacterial Dextranase", *Enzymes of Complex Saccharide Utilization*, vol. 105: pp. 615–621 (1966).

Bartling, G., et al., "Separation of Trypsin and Peroxidase by Ultrafiltration Using Crosslinked Soybean Trypsin Inhibitor", *Biotechnology and Bioengineering*, vol. XVII, pp. 1023–1027 (1976).

Mattiasson, B., et al., "Isolation of Concanavalin A From Seeds of *Conavalia Ensiformis*", *Journal of Chromatography*, vol. 283, pp. 323–330 (1984).

Weiner, C., et al., "Affinity Cross–Flow Filtration: Purification of IgG with a Novel Protein A Affinity Matrix Prepared from Two–Dimensional Protein Crystals", *Biotechnology and Engineering*, vol. 44, pp. 55–65 (1994).

Ghosh, R., et al., "Modeling and Simulation of the Washing Phase of an Affinity Ultrafiltration Sysetm", *Separation Science and Technology*, vol. 31(1) pp. 125–131 (1996).

Luong, J.H.T., et al., "Synthesis and Characterization of a Water–Soluble Affinity Polymer for Trypsin Purification", *Biotechnology and Bioengineering*, vol. 31, pp. 439–446 (1988).

Luong, J.H.T., et al., "A Continuous Affinity Ultrafiltration Process for Trypsin Purification", *Biotechnology and Bioengineering*, vol. 31, pp. 516–520 (1988).

Mattiasson, B., et al., "Ultrafiltration Affinity Purification, A Process for Large–Scale Biospecific Separations", *Ultrafiltration Affinity Purification*, pp. 99–114, (1989).

Male, K.B., et al., "Isolation of Urokinase by Affinity ultrafiltration", *Biotechnoology and Bioengineering*, vol. 35, pp. 87–93 (1990).

Adamski–Medda, D., et al., "Biospecific Ultrafiltration: A Promising Purification Technique for Proteins", *Journal of Membrane Science*, vol. 9, pp. 337–342 (1981).

Mattiasson, B., et al., "Ultrafiltration Affinity Purification", *Annals New York Academy of Science*, vol. 413, pp. 307–309 (1983).

*Primary Examiner*—Keith D. MacMillan
*Assistant Examiner*—P. Ponnaluri
*Attorney, Agent, or Firm*—Deirdre L. Conley

[57] ABSTRACT

The present invention is directed to novel methods for enhancing the ability to separate a species of interest from other different species present in a free solution mixture thereof which takes advantage of interactions that occur between soluble, small molecular weight ligands and the species of interest. The small molecular weight ligands employed in the present invention function to interact with a species of interest in a mixture of different species through either affinity, hydrophobic and/or ionic interactions, thereby altering the molecular weight, hydrodynamic volume and/or isoelectric point of the species of interest and rendering it separable from other component(s) in the mixture.

9 Claims, 9 Drawing Sheets

FIG._9 ns include,
FREE SOLUTION LIGAND INTERACTION MOLECULAR SEPARATION METHOD

FIELD OF THE INVENTION

The present invention relates to methods for the purification and separation of species, particularly those of biological interest, from free solutions wherein the methods employ soluble, small molecular weight ligands that are capable of specifically interacting with the species of interest.

BACKGROUND OF THE INVENTION

The success of many research projects in the biotechnology arts is absolutely dependent upon the availability of techniques that allow for the separation and purification of one or more molecules of interest from complex mixtures comprising those molecules of interest. In this regard, several techniques are currently available for separating and purifying molecules of biological interest, such as proteins, from complex mixtures thereof. These techniques include, for example, affinity chromatography, ion exchange chromatography (IEC), size exclusion chromatography (SEC), high performance liquid chromatography (HPLC), hydrophobic interaction chromatography (HIC), different variations of membrane filtration such as ultrafiltration, microfiltration, reverse osmosis, and the like. However, while these separation techniques have proven useful in a variety of applications, there are often many more applications for which their use is limited.

In an effort to enhance the separation capabilities of these techniques, researchers have developed a number of similar molecular separation techniques, but which are based at least in part upon the ability of an affinity molecule to bind to a entity of interest, thereby rendering that entity of interest separable from the other components of a fluid mixture. One such affinity molecule-based separation technique is affinity chromatography, which separates biological molecules based upon their ability to specifically and selectively bind to an affinity matrix or gel. Affinity gels typically consist of a ligand-binding moiety immobilized on a gel support. For example, GB 2,178,742 utilized affinity chromatography to purify hemoglobin and its chemically modified derivatives based upon the fact that native (oxy)hemoglobin binds specifically to polyanionic functionalities of certain affinity gels. In this process, unmodified hemoglobin is retained by the affinity gel while modified hemoglobin, which cannot bind to the gel because its polyanion binding site is covalently occupied by a modifying agent, is eluted.

However, while affinity chromatography has proven useful for a variety of applications, there are inherent limitations to the technique. For example, because affinity chromatography is dependent upon the attachment of a ligand to a solid phase matrix (such as a polymer bead or other type of polymeric matrix), there exist significant conformational constraints on the attached ligand molecule as well as on the protein which becomes bound to the matrix-attached ligand molecule. Moreover, the solid phase matrix provides a potential site for non-specific binding of various components of a reaction mixture, thereby often resulting in less than completely efficient separations. Also, the overall capacity of an affinity chromatography system is limited by the available surface area of the solid phase and by the density to which that surface area may be substituted by ligand.

Another well known affinity molecule-based separation technique is affinity ultrafiltration, a technique that combines affinity binding with membrane-based ultrafiltration. More specifically, affinity ultrafiltration employs a large, polymeric affinity ligand to which a protein of interest is able to bind followed by ultrafiltration-based separation of the complexed polymeric affinity ligand from the remaining components of a mixture. (See, e.g., Mattiasson et al., *Journal of Chromatography* 283:323–330 (1984), Luong et al., *Biotechnology and Bioengineering* 31:516–520 (1988) and Male et al., *Biotechnology and Bioengineering* 35:87–93 (1990)). However, because large, polymeric affinity ligands are employed as the affinity binding molecule, significant limitations exist as to the separation capacity due to the inherent insolubility of such affinity ligands. Moreover, polymeric affinity ligands are often not readily available and provide relatively low yields and/or purification factors.

van Eijndhoven et al., *Biotechnology and Bioengineering* 48:406–414 (1995) have demonstrated that alterations in the ionic strength of a protein-containing solution may function to alter the apparent size of a protein in that solution. More specifically, van Eijndhoven et al. have demonstrated that the interaction of monovalent ions (such as $Cl^-$) with a protein such as bovine serum albumin may function to alter the hydrodynamic volume of the protein. However, it is currently unknown whether the binding of small monovalent ions to proteins provides a significant enough of a change in the hydrodynamic volume of the protein to render it separable from other similarly sized proteins in a complex mixture thereof using known separation techniques.

There is, therefore, a need to develop novel methods for separating and purifying species of interest from complex free solution mixtures which are not subject to the limitations inherent in other known affinity molecule-based separations. Specifically, there is a need for affinity molecule-based techniques which are not subject to the conformational constraints and non-specific binding problems associated with affinity chromatography. Moreover, there is also a need for novel affinity molecule-based techniques which are not subject to the above described limitations of the affinity ultrafiltration process. The present invention provides a solution to many of these problems.

SUMMARY OF THE INVENTION

The present invention is directed to novel methods for separating a species of interest from other different species present in a free solution mixture thereof which takes advantage of affinity and other interactions that occur between soluble, small molecular weight ligands and a species of interest. Specifically, the present invention is directed to a method for separating a first species of interest from a second species of interest in a free solution mixture comprising the first and second species of interest, where the first and second species of interest are different. The herein described method comprises the step of contacting the free solution mixture with a small molecular weight soluble ligand that interacts in free solution with the first species of interest but not to a significant extent with the second species of interest, thereby forming a first species of interest/ligand complex which is capable of being separated from the second species of interest by a variety of different molecular separation techniques including, for example, size exclusion chromatography and membrane filtration. The small molecular weight ligand has a smaller molecular weight than the first species of interest with which it interacts.

In particular embodiments, the first species of interest may be, for example, a protein or polypeptide (naturally or recombinantly produced), an amino acid, a colloid, an endotoxin, a virus, a nucleic acid, and the like. Small molecular weight ligands which find use in the present invention are soluble in free solution systems and include, for example, proteins, peptides, antibodies, nucleic acids, amino acids, organic and inorganic molecules, multi-ionic molecules, and the like. Typically, the interaction between the first species of interest and the ligand occurs through affinity, hydrophobic and/or ionic interactions.

In various embodiments of the present invention, the first and second species of interest may initially have about the same hydrodynamic volumes, molecular weights and/or isoelectric points, thereby rendering them difficult to separate with conventional separation techniques. One or more of these properties, however, may become different upon interaction by the ligand with the first species of interest. In cases where the hydrodynamic volume of the first species of interest/ligand complex and the second species of interest is about the same, one may often alter the pH or the ionic strength of the system to effectively increase the difference in the hydrodynamic volume between the first species of interest/ligand complex and the second species of interest, thereby enhancing the ability to separate them using conventional separation techniques.

In yet other embodiments of the present invention, one may dissociate and separate the first species of interest and ligand components of the complex which is initially separated from the second species of interest, thereby providing a relatively pure preparation of the first species of interest. Methods for inducing this dissociation generally include altering the pH of the system, altering one or more soluble components in the system, and the like.

Still other embodiments of the present invention will become apparent to the ordinarily skilled artisan upon a reading of the present specification.

BRIEF DESCRIPTION OF THE DRAWINGS

FIG. 1. Elution of Recombinant Humanized IgG (rhulgG) Off a Superdex 200 Size Exclusion Chromatography Column.

FIG. 2. Elution of Sulfhydryl Modified Bovine Serum Albumin (BSA) Off a Superdex 200 Size Exclusion Chromatography Column.

FIG. 2 shows the elution profile of BSA off of a Superdex 200 size exclusion chromatography column. The BSA protein was loaded onto the column at a concentration of 0.3 mg/ml in a buffer of 0.025 M NaCl, 0.025 M Tris base, 0.005 M EDTA, pH 7.1±0.1 and with a load volume of 0.2%. Data is plotted as UV absorbance units (mAU) versus time in minutes (min).

FIG. 3. Elution of a Mixture of Recombinant Humanized IgG (rhulgG) and Sulfhydryl Modified Bovine Serum Albumin (BSA) Off a Superdex 200 Size Exclusion Chromatography Column.

FIG. 4. Elution of a Recombinant Humanized IgG (rhulgG)/Recombinant Protein A (rPrA) Complex Off a Superdex 200 Size Exclusion Chromatography Column.

FIG. 5. Elution of Recombinant Protein A (rPrA) Off a Superdex 200 Size Exclusion Chromatography Column.

FIG. 6. Elution of a Mixture of a Recombinant Humanized IgG (rhulgG)/Recombinant Protein A (rPrA) Complex and Sulfhydryl Modified Bovine Serum Albumin (BSA) Off a Superdex 200 Size Exclusion Chromatography Column.

FIG. 7. Elution of Recombinant Humanized IgG (rhulgG) Off a Superose 6 Size Exclusion Chromatography Column.

FIG. 8. Elution of Recombinant Protein A (rPrA) Off a Superose 6 Size Exclusion Chromatography Column.

FIG. 9. Elution of a Recombinant Humanized IgG (rhulgG)/Recombinant Protein A (rPrA) Complex Off a Superose 6 Size Exclusion Chromatography Column at pH 3.5.

DETAILED DESCRIPTION OF THE INVENTION

A. Definitions

As used herein, the phrases "species" or "species of interest" generally mean a particle(s) or molecule(s) that is to be separated from a free solution or fluid mixture, for example, a liquid. The species are separated from the free solution mixture and, in most instances, from other particles, molecules or species present in the mixture. Preferably, species of interest are biological entities of natural, biological or biochemical origin or produced by biological or biochemical processes. Examples of preferred species of interest include, without being limiting of the invention, molecules such as, for example, polypeptides, either naturally or recombinantly produced, proteins, either naturally or recombinantly produced, cellular components, nucleic acids, including both DNA and RNA, colloids, mycoplasm, endotoxins, viruses, bacteria, carbohydrates, and various other biological molecules or interest, whether glycosylated or not. One or more species of interest may be an "impurity" meaning that it is a component that is an undesirable component of a mixture and which is to be separated from the mixture. Species of interest may also be fusion proteins where at least a portion of the fusion protein is a polypeptide for which at least one small molecular weight ligand is readily available. For example, the first species of interest may be a protein comprising an immunoglobulin-derived polypeptide to which the Protein A ligand has specific binding affinity.

As used herein, a "mixture" of species refers to a free solution (for example, a liquid) or suspension which contains two or more different species. The types of species present in any mixture and their abundance in the mixture may differ greatly, wherein a mixture may contain, for example, various different polypeptides, buffers, salts, cells and cell components, and the like. Mixtures may be complex, wherein a large number of different species are represented, or relatively simple, where only a small number of different species are represented.

As used herein, the term "ligand" refers to a molecule which is soluble in free solution (i.e., has some degree of solubility in the solution) and is capable of interacting with a species of interest to alter at least one of the physical properties of the species with which the ligand interacts. Ligands which find use herein are such that one or more may interact with a single molecule of the species of interest. By "interacting" with a species of interest is meant that the ligand is (or multiple ligands are) capable of physically binding, either reversibly or irreversibly, to the species of interest or otherwise altering one or more of the physical properties of the species, including, for example, hydrodynamic volume, molecular weight, isoelectric point, and the like. Often, the interaction between the first species of interest and the ligand is "specific", meaning that the ligand "preferentially interacts with" or "preferentially binds to" the first species of interest as compared to with any other entity present in the mixture. By "preferential" interaction or binding is meant that the ligand interacts or binds to a greater extent to the first species of interest than to any other species in the free solution. Generally, a "preferentially" binding ligand interacts with a species of interest at least about 2-fold more effectively than with other species present in the solution, preferably at least about 5-fold more effectively and more preferably at least about 10-fold more effectively in terms of binding affinity and/or residence time. In some cases, the ligand may interact with other components of the free solution mixture, however, it may interact with the first species of interest to a greater extent (e.g., more ligand molecules per species molecule), thereby resulting in the desired change in molecular weight, hydrodynamic volume and/or isoelectric point.

Ligands which find use in the present invention are "small molecular weight" ligands meaning that they are smaller in terms of molecular weight than the first species of interest with which they interact. In this regard, by "smaller" is meant that the molecular weight of the ligand is from about 0.5 to 99.5% of that of the species with which it interacts, preferably from about 5 to 90%, more preferably from about 10 to 80°, and usually from about 20 to 75% of the molecular weight of the species with which it interacts. Ligands that find use in the present invention (are capable of interacting with the first species of interest through affinity, hydrophobic and/or ionic interactions and include, for example, proteins, including antibodies, peptides, nucleic acids, saccharides, amino acids, organic and inorganic molecules, multi-ionic molecules (i.e., molecules possessing more than one ionic group), and the like. The term "ligand" as defined herein is not intended to encompass monovalent ionic species such as protons, metal ions, and the like.

Ligands which find use in the present invention may be known and available to the ordinarily skilled artisan or may be readily identified using routine screening techniques. For example, one may screen combinatorial oligopeptide or oligonucleotide libraries to identify library members which are capable of interacting with the first species of interest, thereby allowing the identification of ligands which potentially will find use in the present invention. Those library members which interact with the first species of interest can then be optionally screened for the inability to interact with the second species of interest. In this regard, it is noted that techniques for preparing and screening combinatorial libraries for members capable of interacting with a target molecule are well known in the art.

By "species of interest/ligand complex" or grammatical equivalents thereof is meant the complex that is formed when one or more small molecular weight ligands interact with a species of interest, thereby altering the molecular weight, hydrodynamic volume and/or isoelectric point of the species of interest and, in turn, rendering it capable of being separated from other species present in a free solution mixture. By "capable of being separated" or grammatical equivalents thereof is meant that molecular separation techniques which are currently known or which may be developed in the future are capable of separating the first species of interest/ligand complex from the second species of interest to provide a composition that is essentially free of the second species of interest. By "essentially free" is meant that the second species of interest is either absent in the composition or is present in the composition to an extent that does not interfere with any desired function of the purified first species of interest. The individual components of a species of interest/ligand complex are often capable of dissociation, thereby allowing for the separation and purification of those individual components after the complex is separated from other components present in a fluid mixture.

With respect to species of interest and ligands, the term "separating" means that a component or components are purified away from other component(s) present in a fluid mixture. Various molecular separation techniques are known in the art and will find use herein, including membrane filtration and chromatography techniques.

As used herein, the phrase "membrane filtration" refers to all types of filtration processes which employ a porous membrane or membranes to separate molecules of different relative sizes. Different types of membrane filtration processes are known in the art and include, for example, high performance tangential flow filtration, ultrafiltration, reverse osmosis and microfiltration.

As used herein, the phrases "tangential flow filtration" or "TFF" refer to a process in which the free solution mixture containing the components to be separated by membrane filtration is recirculated tangential to the plane of the filtration membrane to increase the mass-transfer coefficient for back diffusion. In such membrane filtrations, a pressure differential is applied along the length of the filtration membrane to cause the solution and filterable solutes to flow through the membrane. This membrane filtration is suitably conducted as a batch process as well as a continuous flow process. For example, the solution may be passed repeatedly over the filtration membrane while that fluid which passes through the membrane is continually drawn off into a separate unit or the solution is passed once over the filtration membrane and the fluid passing through the membrane is continually processed downstream.

As used herein, the phrases "high performance tangential flow filtration" or "HPTFF" refer to the membrane filtration process that is described in U.S. Pat. Nos. 5,256,294 and 5,490,937, both of which are expressly incorporated herein by reference in their entirety.

As used herein, the terms "ultrafiltration" or "UF" refer to membrane filtration processes which employ filtration membranes rated for retaining solutes having a molecular weight between about 1 kDa and 1000 kDa.

As used herein, the phrases "reverse osmosis" or "RO" refer to membrane filtration processes which employ membranes capable of retaining solutes of a molecular weight of less than about 1 kDa, such as salts and other low molecular weight solutes.

As used herein, the terms "microfiltration" or "MF" refer to membrane filtration processes which employ membranes in the 0.1 to 10 micron pore size range.

As used herein, the phrase "size exclusion chromatography" refers to a well known process by which one employs chromatographic techniques to separate at least one molecule from at least another molecule on the basis of size. For the presently claimed methods, size exclusion chromatography is generally performed at low ionic strengths, for example, less than about 150 mM, preferably less than about 100 mM and more preferably less than about 75 mM, usually less than about 50 mM.

B. Modes For Practicing the Invention

In its broadest aspect, the present invention is directed to methods for separating of a first species of interest from a different second species of interest in a free solution mixture which comprises both the first and second species of interest. The method comprises contacting the free solution mixture with a small molecular weight ligand which is soluble in free solution and which is capable of interacting with the first species of interest to form a first species of interest/ligand complex in free solution, thereby altering at least one of the physical properties of the first species of interest. Preferably, by interacting with the first species of interest, the ligand functions to increase the hydrodynamic volume, the molecular weight and/or change the isoelectric point of the first species of interest, thereby rendering it capable of being separated from the second species of interest by well known separation techniques. The present invention finds particular use in situations where the first and second species of interest are initially incapable of being efficiently separated because, for example, they have similar hydrodynamic volumes, molecular weights and/or isoelectric points. In such cases, the first species of interest may interact with the ligand, thereby increasing the hydrodynamic volume thereof and rendering it capable of being separated (as a complex) from the second species of interest. The first species of interest may then be dissociated and separated from the ligand to provide a pool of pure first species of interest which is essentially free of the ligand and the second species of interest.

The ligand may be introduced into the system by various means, none of which will be critical to the present invention. Preferably, the ligand will be introduced directly into a free solution mixture which comprises both the first and second species of interest. In such situations, the ligand will be capable of preferentially interacting with the first species of interest as compared to the second. The ligand may be introduced into the free solution mixture as a single bolus or may be added in multiple steps over an extended period of time.

As described above, the first and second species of interest may be any of a number of different entities, biological or otherwise, and may include molecules such as, for example, polypeptides, either naturally or recombinantly produced, proteins, either naturally or recombinantly produced, including fusion proteins, cellular components, nucleic acids, including both DNA and RNA, colloids, mycoplasm, endotoxins, viruses, bacteria, carbohydrates, and various other biological molecules or interest, whether glycosylated or not. Preferably, the first species of interest is a recombinantly produced protein.

Ligands which find use in the present invention will be soluble in free solution (meaning that they possess at least some degree of solubility in the system) and will have a smaller molecular weight than the first species of interest for which they are capable of interacting. For the most part, the ligand entity will be capable of non-covalently binding to the first species of interest and will generally be a protein, such as an antibody, a peptide, a nucleic acid, a saccharide, an amino acid, an organic or inorganic molecule, a multi-ionic molecule, and the like, specifically excluding such monovalent entities as protons and metal ions. Ligands which find use in the present invention will be readily available, either commercially or will be capable of being readily synthesized and identified in a routine manner, such as through the preparation and screening of combinatorial libraries. In cases where the ligand of choice is a protein, the protein will be commercially available, such as protein A, or will be readily prepared by recombinant DNA expression techniques.

In cases where the ligand is an antibody which is capable of specifically binding to the first species of interest, such antibodies will be capable of being prepared and screened for the desired binding specificity by routine technology. For example, one of ordinary skill in the art is capable of quickly, easily and routinely obtaining either a polyclonal or monoclonal antibody preparation that is directed against any protein of interest. Polyclonal antibodies to the protein are generally raised in animals by multiple subcutaneous (sc) or intraperitoneal (ip) injections of the protein in combination with an adjuvant. It may be useful to conjugate the protein or fragment of interest to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Host animals may then be immunized against the immunogenic conjugates or derivatives by combining the conjugate with an appropriate adjuvant and injecting the solution intradermally at multiple sites. One month later, the animals may be boosted with 1/5 to 1/10 the original amount of conjugate in appropriate adjuvant by subcutaneous injection at multiple sites. 7 to 14 days later the animals may be bled and the serum assayed for the presence of anti-protein of interest antibody titer. Animals may be boosted until the titer plateaus. Also, aggregating agents such as alum may be employed to enhance the immune response. Polyclonal antibodies are then purified from the immune serum using conventional techniques.

Monoclonal antibodies directed against the protein of interest may be obtained from a population of substantially homogeneous antibodies, i.e., the individual antibodies comprising the population are identical except for possible naturally-occurring mutations that may be present in minor amounts. For example, monoclonal antibodies directed against a protein of interest may be made using the hybridoma method first described by Kohler & Milstein, *Nature* 256:495 (1975) or may be made by recombinant DNA methods (Cabilly et al., U.S. Pat. No. 4,816,567).

In the hybridoma method, a mouse or other appropriate host animal, such as hamster is immunized to elicit lymphocytes that produce or are capable of producing antibodies that will specifically bind to the protein used for immunization. Alternatively, lymphocytes may be immunized in vitro. Lymphocytes may then be fused with myeloma cells using a suitable fusing agent, such as polyethylene glycol, to form a hybridoma cell (Goding, *Monoclonal Antibodies: Principles and Practice*, pp.59–103 (Academic Press, 1986)).

The hybridoma cells thus prepared may then be seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.* 133:3001 (1984) and Brodeur et al., *Monoclonal Antibody Production Techniques and Applications*, pp.51–63 (Marcel Dekker, Inc., New York, 1987)).

Culture medium in which hybridoma cells are growing is then assayed for the production of monoclonal antibodies directed against the protein of interest. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibodies can, for example, be determined by the Scatchard analysis of Munson & Pollard, *Anal. Biochem.* 107:220 (1980).

Ligands which are oligonucleotides may be chemically synthesized by known methods such as phosphotriester, phosphite, or phosphoramidite chemistry, using solid phase techniques such as those described in EP 266,032, published May 4, 1988, or via deoxynucleoside H-phosphonate intermediates as described by Froehler et al., *Nucl. Acids Res.* 14:5399 (1986). Following synthesis, the oligonucleotide probes may then be purified on polyacrylamide gels. Ligands which are peptides may be synthesized by employing standard Merrifield solid phase synthetic methods, manually or by using an automated peptide synthesizer, standard protection chemistry (e.g., t-Boc or Fmoc chemistry) and resins (e.g., 4-methyl benzhydryl amine or Rink Amide resin). Successive rounds of deprotection of the terminal amino group and coupling of amino acid monomers, followed by deprotection and cleavage of peptides from resins results in the synthesis of oligopeptides of the desired sequence and length. Additionally, liquid phase peptide synthesis is well known in the art and may also be employed. Combinatorial oligonucleotide or oligopeptide libraries may be prepared using conventional combinatorial technology and those libraries screened to identify library members which may function as small molecular weight ligands in the presently described methods, wherein such methodology is well known in the art.

When present in a fluid mixture, the first and second species of interest may be effectively separated by contacting the fluid mixture with a small molecular weight ligand that is capable of interacting with the first species of interest but not with the second species of interest (or with the second species of interest but to a lesser extent). The method is particularly useful in situations where the first and second species of interest have approximately the same size, hydrodynamic volume and/or isoelectric point, thereby rendering them difficult to separate using conventional molecular separation techniques. However, by interacting with the first species of interest, the ligand functions to increase the molecular weight and/or hydrodynamic volume of the first species of interest (and/or alter the isoelectric point of the first species of interest), thereby rendering it capable of being separated by conventional molecular separation techniques.

Generally, the hydrodynamic volume of a species of interest is determined by size exclusion chromatography; a technique which is well known in the art. By having a hydrodynamic volume which is "about the same" as another different species of interest, the two species of interest have hydrodynamic volumes which are within about 10% of each other.

The isoelectric point of a species of interest is the pH at which the species is electrically neutral. The isoelectric point of a species of interest may be determined by conventional techniques that subject the species to both a pH gradient and an electrical field and determining at what pH the species is electrically neutral, i.e., determining at what pH the species does not migrate towards one direction or another in an electric field. By having an isoelectric point which is "about the same" as another species of interest, the isoelectric points of the two species are within about 0.5 pH points of one other.

In certain embodiments of the present invention, one may further enhance the ability to separate the first and second species of interest byf altering the pH or ionic strength of the fluid mixture. This step finds particular use in situations where the first species of interest/ligand complex possesses a hydrodynamic volume which is about the same as that of the second species of interest. By altering the pH and/or ionic strength of the system, one may alter the apparent size (in terms of hydrodynamic volume or molecular weight) of a protein or protein complex by a factor of up to about 10-fold (see, e.g., Pujar and Zydney, "Analysis of Electrostatic Interactions on Protein Sieving: Experimental and Theoretical Investigations", North America Membrane Society Meeting, Ottawa, Canada, 1996. By increasing the difference in hydrodynamic volume between the first species of interest/ligand complex and the second species of interest (or the first and second species of interest) by altering the pH and/or ionic strength of the fluid mixture, one can more effectively separate the first and second species of interest using conventional molecular separation techniques.

Once the small molecular weight ligand is allowed to interact with the first species of interest in the fluid mixture, the first species of interest/ligand complex may be separated from the second species of interest using conventionally employed molecular separation techniques. For example, the step of separating the components may comprise the use of conventional membrane filtration techniques such as tangential flow filtration, high performance tangential flow filtration, ultrafiltration, microfiltration and reverse osmosis. The first species of interest/ligand complex and second species of interest may also be separated using conventional chromatographic techniques including, for example, SEC, HPLC, and the like. Once the first species of interest/ligand complex is separated from the second species of interest, the components of the complex may be dissociated and separated using one of the same techniques described above for separation of the complex from the second species of interest. The complex may be dissociated by any treatment which disrupts the interaction between the two molecules, for example, by lowering the pH of the system in which they exist or by the addition to the system of any component which causes the first species of interest to dissociate from the ligand.

The presently described method is useful for virtually any application which requires that one entity of a mixture be separated from another entity present in the mixture. Preferred applications include, for example, the separation and purification of one or more proteins from a complex mixture of different proteins, especially during large scale recombinant protein production. The methods of the present invention are applicable for separation and purification of a wide range of biological molecules, e.g., proteinaceous products of fermentation of natural or genetically engineered microorganisms, polypeptides, antibodies, cellular secretions, colloids, mycoplasm, endotoxins, viruses, bacteria, amino acids, DNA, RNA, carbohydrates, and the like.

The present invention has a number of advantages over the existing prior art. For example, the presently described method is advantageous over standard solid matrix affinity chromatography methods in that it employs ligands of small molecular weight that are soluble in free solution. As such, while in affinity chromatography there are conformational constraints on both the ligand and the species to which it binds, such is not the case with the presently described methods. Moreover, the separation capacity of an affinity chromatography system is limited by the surface area of the solid matrix employed and the density to which that surface area may be substituted with ligand. To the contrary, the separation capacity of the presently described methods are limited only by the solubility of the ligand in the fluid mixture. Moreover, the presence of the solid matrix in an affinity chromatography system provides significant opportunity for non-specific protein-matrix interactions, thereby resulting in less than efficient molecular separations.

The presently described method is also advantageous over affinity ultrafiltration in that the large, polymeric ligands employed in affinity ultrafiltration are often not readily available or capable of being easily synthesized whereas the soluble, small molecular weight ligands employed in the present invention are readily available and/or can be routinely synthesized. Moreover, affinity ultrafiltration is limited to applications which employ ultrafiltration process whereas the present method may be employed with a variety of different molecular separation techniques including, for example, many types of membrane filtration as well as chromatographic methods. Furthermore, affinity ultrafiltration often provides relatively low yields and purification factors due to the limited solubility of many large polymeric ligands in solutions, a problem which is overcome by employing soluble, small molecular weight ligancis as in the present invention.

Further details of the invention are illustrated in the following non-limiting examples.

C. Examples

Example I

Molecular Separation of Recombinant Humanized IgG From a Bovine Serum Albumin Impurity Using a Soluble Protein A Ligand.

The ligand interaction molecular separation method described herein was used to separate recombinant humanized IgG protein from a mixture which also contained a sulfhydryl modified bovine serum albumin protein as an impurity. High performance liquid chromatography (HPLC) SEC was used to identify the individual molecules, as well as, demonstrate complex formation, dissociation, and protein separation from the ligand. The HPLC system consisted of a quaternary pump, auto sampler and injector, ultraviolet absorbance detector, an interface module, computer and Hewlett Packard Chemstation data acquisition and processing software (Model 1050 HPLC, Hewlett Packard, Inc., Palo Alto, Calif.).

The complex was formed using recombinant humanized IgG (rhulgG) as the protein product of interest and recombinant Protein A (rPrA) as the small molecular weight ligand which interacts therewith. Stock solutions were prepared in the mobile phase buffer (0.025 M NaCl, 0.025 M Tris base, 0.005 M EDTA, pH 7.1±0.1) at a concentration of 8 mg/ml and 5 mg/ml, respectively. The stock solutions were combined and diluted in this buffer to form a complex containing 0.8 mg/ml of rhulgG and 0.2 mg/ml of rPrA.

Bovine serum albumin (BSA) monomer was purified from sulfhydryl modified BSA from Miles Corporation using size exclusion chromatography. This monomer was employed as the impurity. A stock solution was prepared in the mobile phase buffer (0.025 M NaCl, 0.025 M Tris base, 0.005 M EDTA, pH 7.1±0.1) at a final concentration of 5 mg/ml.

To form the complex in the presence of the impurity, rPrA was added to a solution of rhulgG and BSA in the mobile phase buffer (0.025 M NaCl, 0.025 M Tris base, 0.005 M EDTA, pH 7.1±0.1) to a final concentration of 0.8 mg/ml rhulgG, 0.2 mg/ml rPrA and 0.3 mg/ml BSA. As a control, to demonstrate the separation of the impurity from the product without the presence of the complex, the rhulgG and BSA stock solutions were combined and diluted in the mobile phase buffer to a final concentration of 0.8 mg/ml and 0.3 mg/ml, respectively.

Samples of the three individual stock solutions, as well as samples of the complex, complex-impurity and protein product-impurity solutions were injected onto size exclusion chromatography (SEC) columns as described below to determine the retention times and separations of the different species.

The above described individual stock solutions and various mixtures thereof were analyzed by size exclusion chromatography as follows. Samples were injected into two Superdex™ 200 columns (inner diameter=10 mm, length=300 mm per column, Pharmacia Biotech Inc., Piscataway, N.J.) which were set up in series. A buffer containing 0.025 M NaCl, 0.025 M Tris base, 0.005 M EDTA, pH 7.1±0.1 was used as the mobile phase. After injection onto the columns, the samples were separated in the columns at a volumetric flow rate of 0.5 ml/minute. The total run time per sample was 90 minutes. Protein elution was measured by ultraviolet absorbance at 280 nm. These parameters are summarized in Table 1.

TABLE 1

| HPLC-SEC Method: Complex-Impurity Separation | |
|---|---|
| Column: | Superdex 200 10/30, two in series (60 cm) |
| | Separation Range: 10,000 to 600,000 Mr |
| | 48 ml total column volume |
| Running Buffer: | Tris base 0.025 M |
| | NaCl 0.025 M |
| | EDTA 0.005 M |
| | pH 7.1 ± 0.1 |
| Flow Rate: | 0.5 ml/minute |
| Run Time: | 90 minutes |
| UV Wavelength: | 280 |

Figure 1:
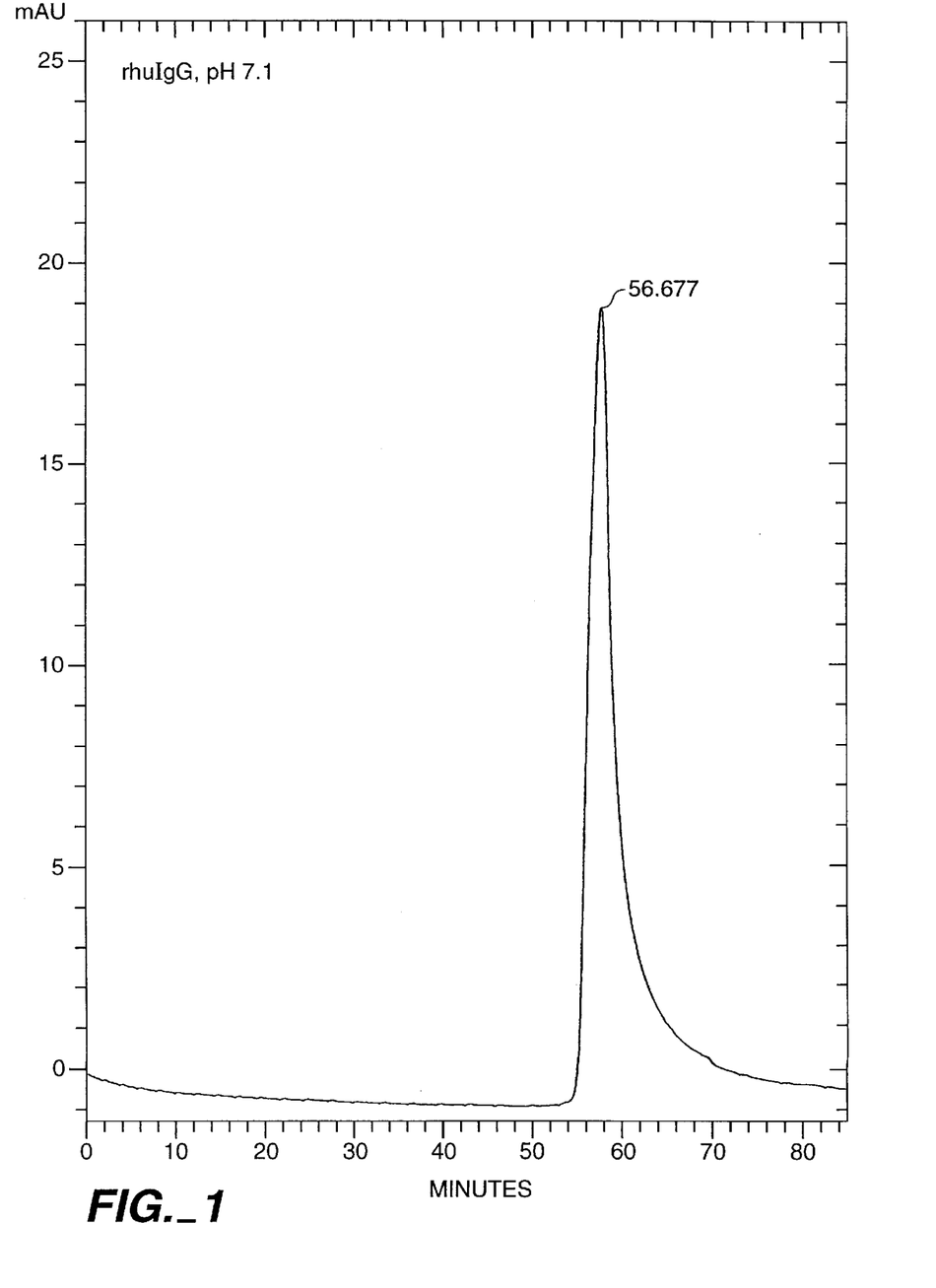
FIG. 1 shows the elution profile of rhulgG off of a Superdex 200 size exclusion chromatography column. The rhulgG protein was loaded onto the column at a concentration of 8 mg/ml in a buffer of 0.025 M NaCl, 0.025 M Tris base, 0.005 M EDTA, pH 7.1±0.1 and with a load volume of 0.04%. Data is plotted as UV absorbance units (mAU) versus time in minutes (min).
Figure 2:
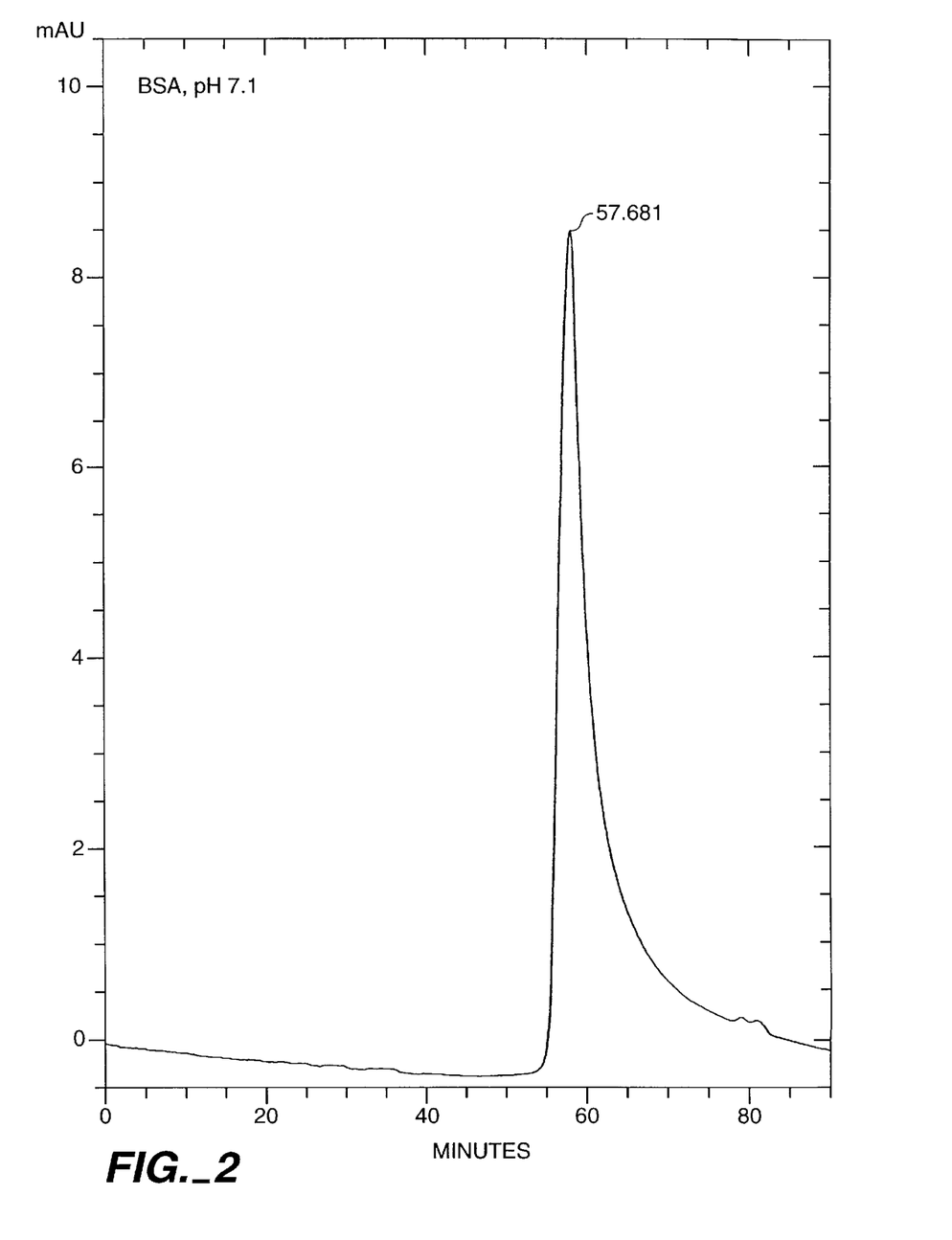
Figure 3:
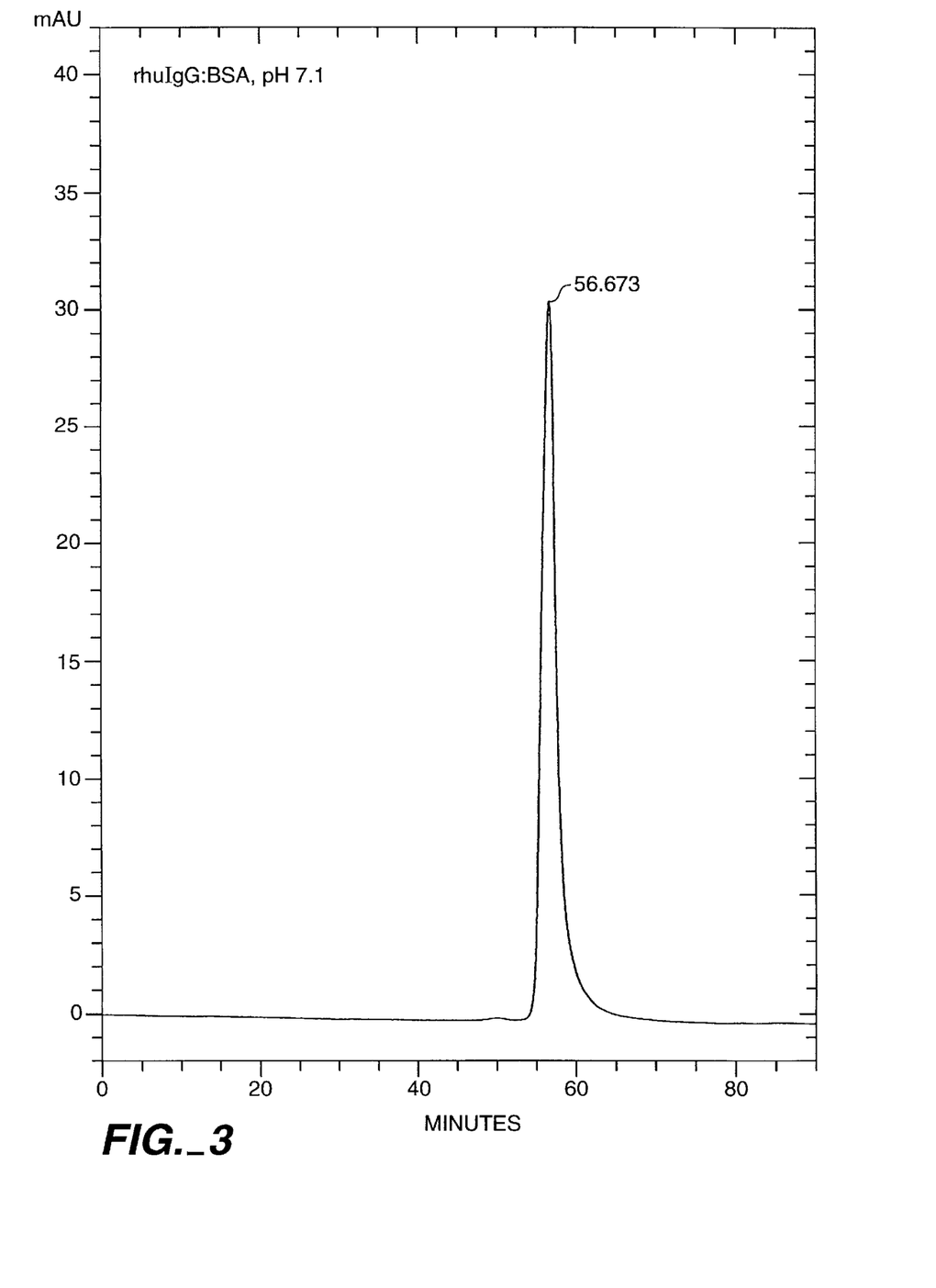
FIG. 3 shows the elution profile of an rhulgG and BSA mixture off of a Superdex 200 size exclusion chromatography column. The rhulgG and BSA proteins were loaded onto the column at a concentration of 0.8 mg/ml and 0.3 mg/ml, respectively, in a buffer of 0.025 M NaCl, 0.025 M Tris base, 0.005 M EDTA, pH 7.1±0.1 and with a load volume of 0.2%. Data is plotted as UV absorbance units (mAU) versus time in minutes (min).

Under the above described separation conditions, separation of the BSA impurity from the rhuIgG product could not be achieved. For example, as shown in FIGS. 1 and 2, the individual BSA and rhuIgG molecules showed very close retention times, 55.9 minutes for rhuIgG (FIG. 1) and 57.7 minutes for BSA (FIG. 2). When a mixture of the rhuIgG and BSA molecules was prepared and analyzed by the above described HPLC-SEC separation method, a single peak was observed with a retention time of 56.7 minutes (FIG. 3), evidencing the inability to separate the desired protein product (rhuIgG) from the impurity (BSA).

Figure 4:
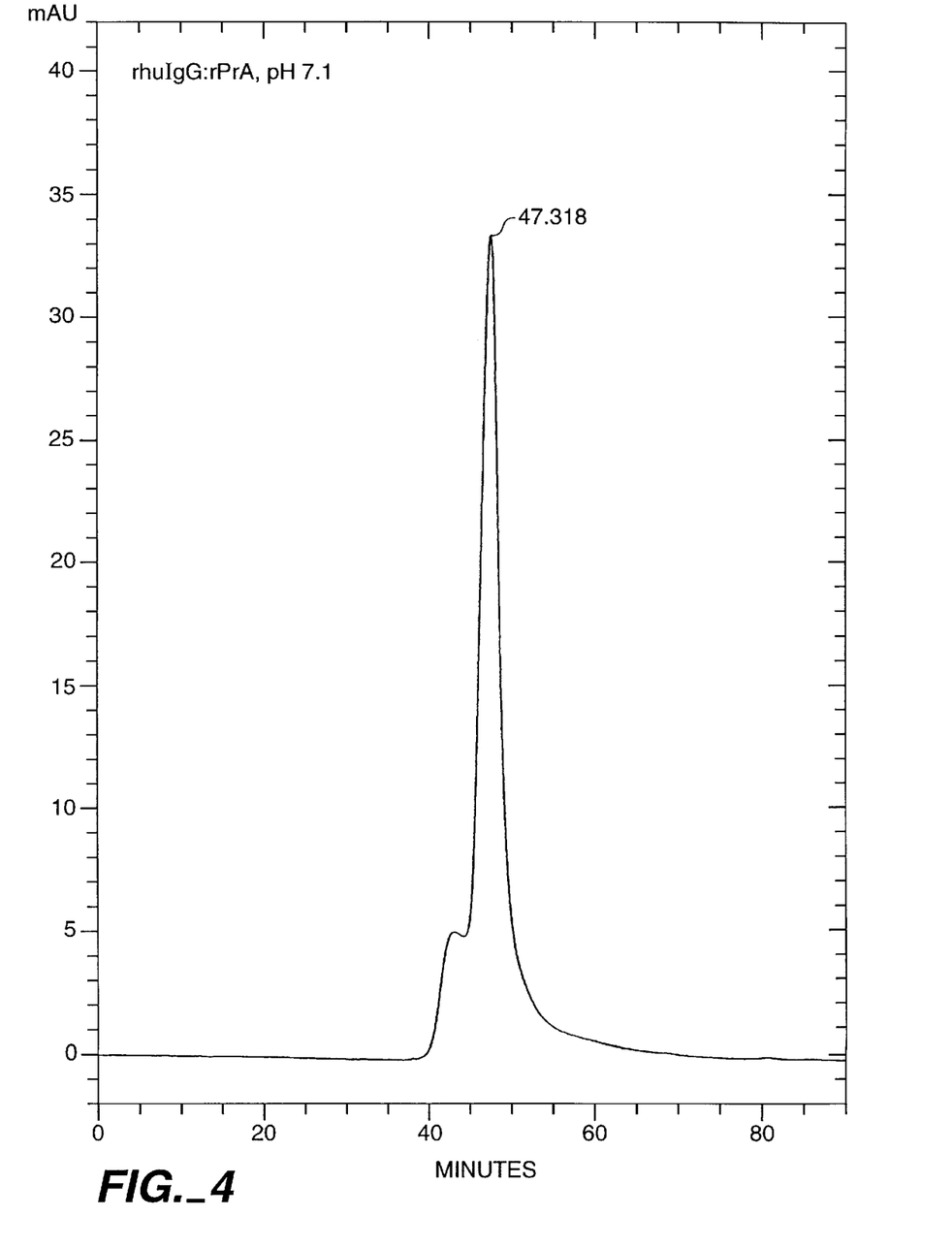
FIG. 4 shows the elution profile of rhulgG/rPrA complex off of a Superdex 200 size exclusion chromatography column. The rhulgG and rPrA proteins were loaded onto the column at a concentration of 0.8 mg/ml and 0.2 mg/ml, respectively, in a buffer of 0.025 M NaCl, 0.025 M Tris base, 0.005 M EDTA, pH 7.1±0.1 and with a load volume of 0.2%. Data is plotted as UV absorbance units (mAU) versus time in minutes (min).
Figure 5:
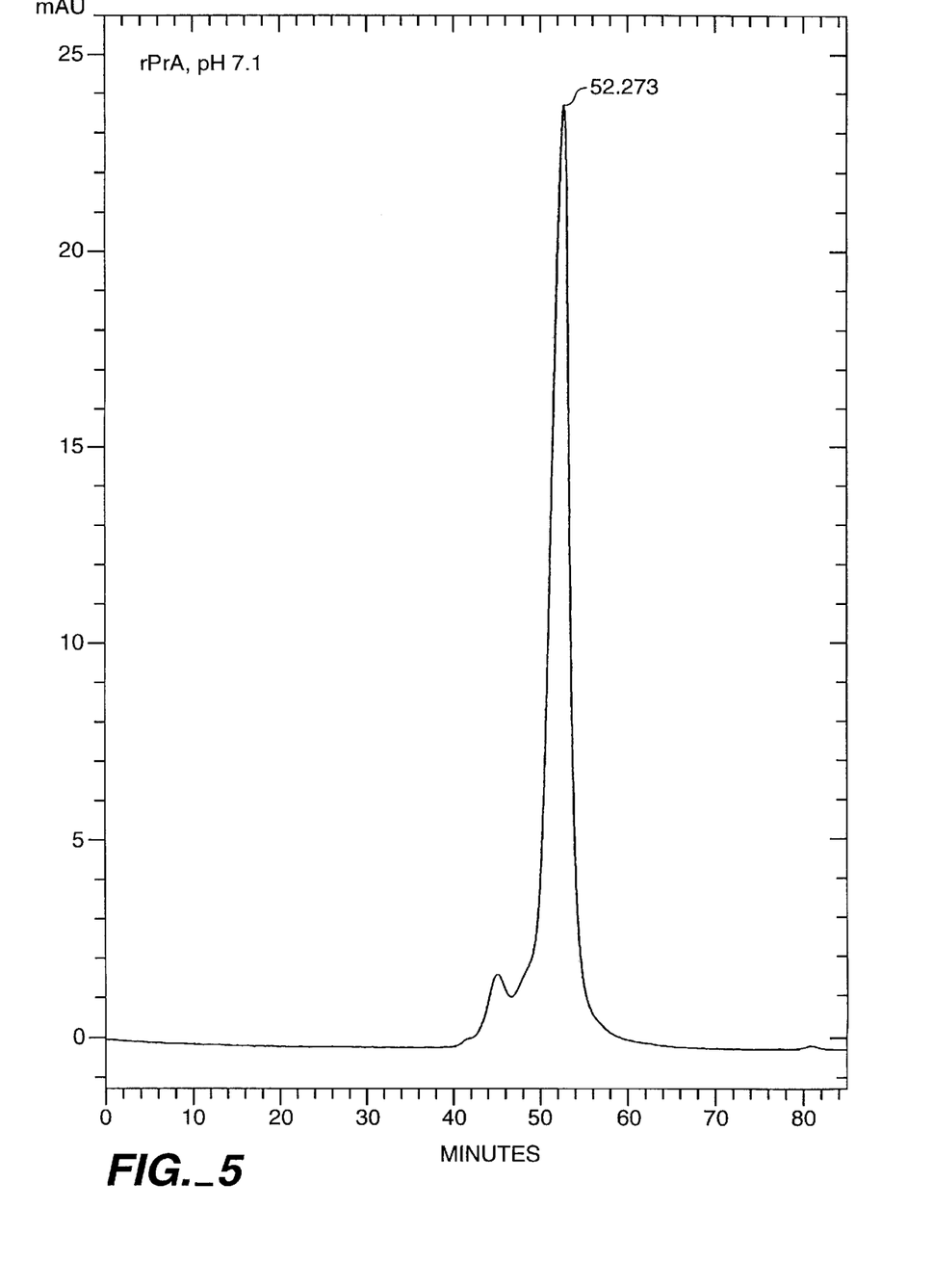
FIG. 5 shows the elution profile of rPrA off of a Superdex 200 size exclusion chromatography column. The rPrA protein was loaded onto the column at a concentration of 2 mg/ml in a buffer of 0.025 M NaCl, 0.025 M Tris base, 0.005 M EDTA, pH 7.1±0.1 and with a load volume of 0.2%. Data is plotted as UV absorbance units (mAU) versus time in minutes (min).

Formation of the rhuIgG/rPrA complex was demonstrated by the HPLC-SEC method described above with a single peak at 47.3 minutes observed upon injection of the solution containing a complex formed from 0.8 mg/ml rhuIgG and 0.2 mg/ml rPrA (FIG. 4). When injected individually, rhuIgG and rPrA had retention times of 55.9 minutes (FIG. 1) and 52.3 minutes (FIG. 5), respectively. The shift to a single peak with a lower retention time than either of the two individual molecules indicates the formation of a complex having a larger molecular weight and hydrodynamic volume.

Figure 6:
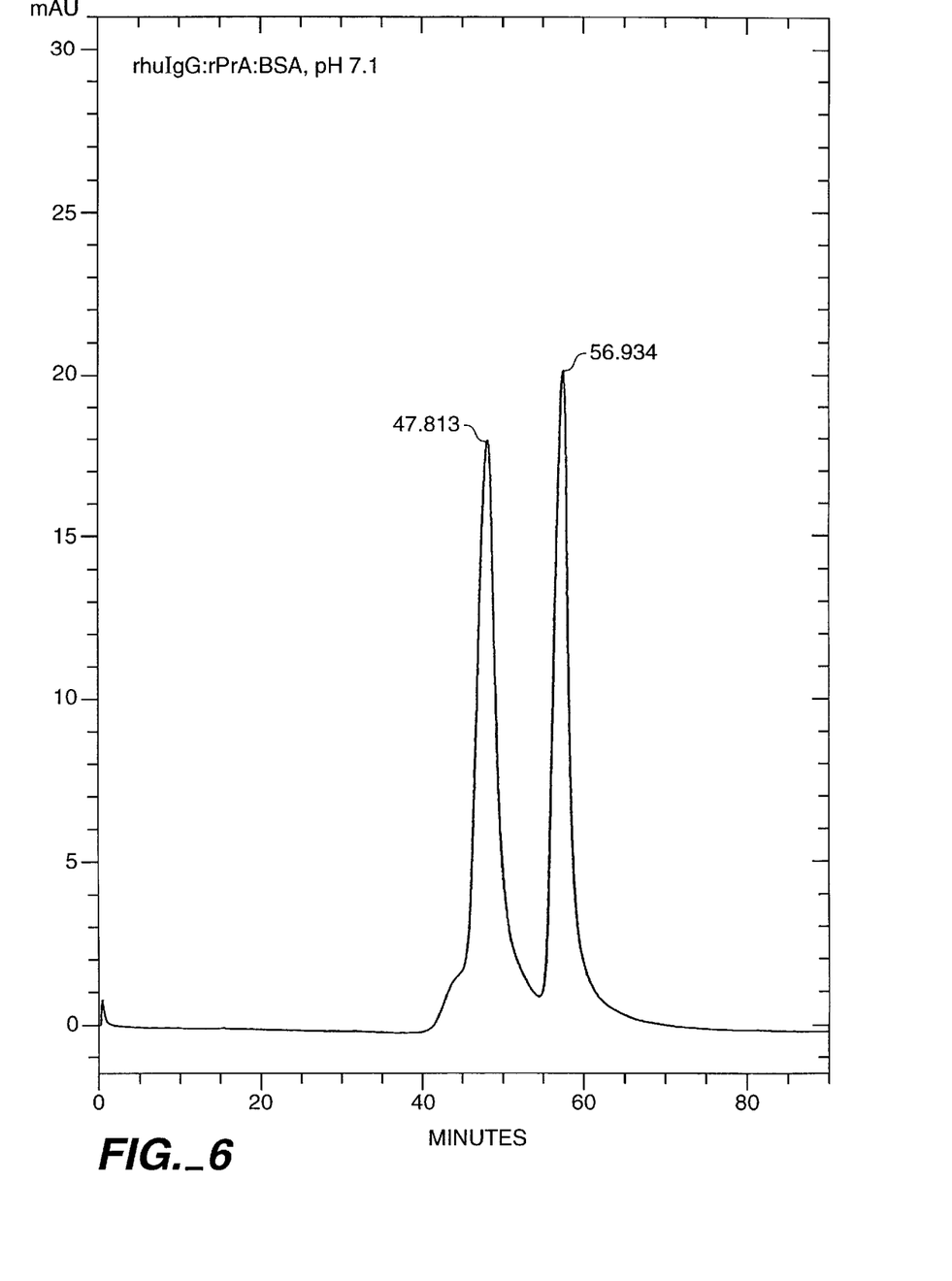
FIG. 6 shows the elution profile of a mixture of rhulgG/rPrA complex and BSA off of a Superdex 200 size exclusion chromatography column. The rhulgG, rPrA and BSA proteins were loaded onto the column at a concentration of 0.8 mg/ml, 0.2 mg/ml and 0.3 mg/ml, respectively, in a buffer of 0.025 M NaCl, 0.025 M Tris base, 0.005 M EDTA, pH 7.1±0.1 and with a load volume of 0.2%. Data is plotted as UV absorbance units (mAU) versus time in minutes (min).

By forming the complex between rhuIgG and rPrA and thereby changing the effective hydrodynamic volume of the protein, separation of the BSA impurity from the rhuIgG/rPrA complex could now be achieved. For example, as shown in FIG. 6, the retention time for the complex was 47.8 minutes whereas the retention time for the clearly distinct BSA impurity was 56.9 minutes. Thus, by introducing a small molecular weight ligand which is capable of interacting with a product protein which thereby alters the effective molecular weight and hydrodynamic volume of the protein product, one may effectively separate the product protein (in the form of complex with a ligand) from an impurity which is not separable from the product protein when individually combined.

After separation of the BSA impurity from the rhuIgG/rPrA complex as described above, the complex was dissociated into its individual components which were then, in turn, separated so as to obtain a pure rhuIgG protein product free of BSA and rPrA. Dissociation of the rhuIgG/rPrA complex into its individual rhuIgG and rPrA components was observed by altering the pH and ionic strength of the solution as follows.

Specifically, two Superose™ 6 columns (inner diameter=10 mm, length=300 mm per column, Pharmacia Biotech, Inc., Piscataway, N.J.) were run in series. A buffer containing 0.1 M acetic acid, 0.15 M NaCl, pH 3.5±0.1 was employed as the mobile phase, at a volumetric flow rate of 0.4 ml/minute. Protein elution was monitored by ultraviolet absorbance at 214 nm. Total run time per sample injected was 110 minutes. These parameters are summarized in Table 2 below.

TABLE 2

| HPLC-SEC Method: Complex Dissociation and Component Separation | |
|---|---|
| Column: | Superose ™ 6 10/30, two in series |
| | Separation Range: 5,000 to 5,000,000 Mr |
| | 48 ml total column volume |
| Running Buffer: | Acetic Acid 0.1 M |
| | NaCl 0.15M |
| | pH 3.5 ± 0.1 |
| Flow Rate: | 0.4 ml/minute |
| Run Time: | 110 minutes |
| UV Wavelength: | 214 nm |

Samples of individual rhuIgG and rPrA stock solutions, as well as the complex solution containing 0.08 mg/ml rhuIgG and 0.2 mg/ml rPrA were injected onto the column to determine retention times and separation, of the different species. The samples were prepared in a running buffer, of 0.025 M NaCl, 0.025 M Tris base, 0.005 M EDTA, pH 7.1±0.1. Since the volume of sample injected was so small compared to the total volume of the column (0.2% load), theoretical calculations showed that the samples were exchanged into the mobile phase of 0.1 M acetic acid, 0.15 M NaCl, pH 3.5±0.1 within the first centimeter of column length.

Figure 7:
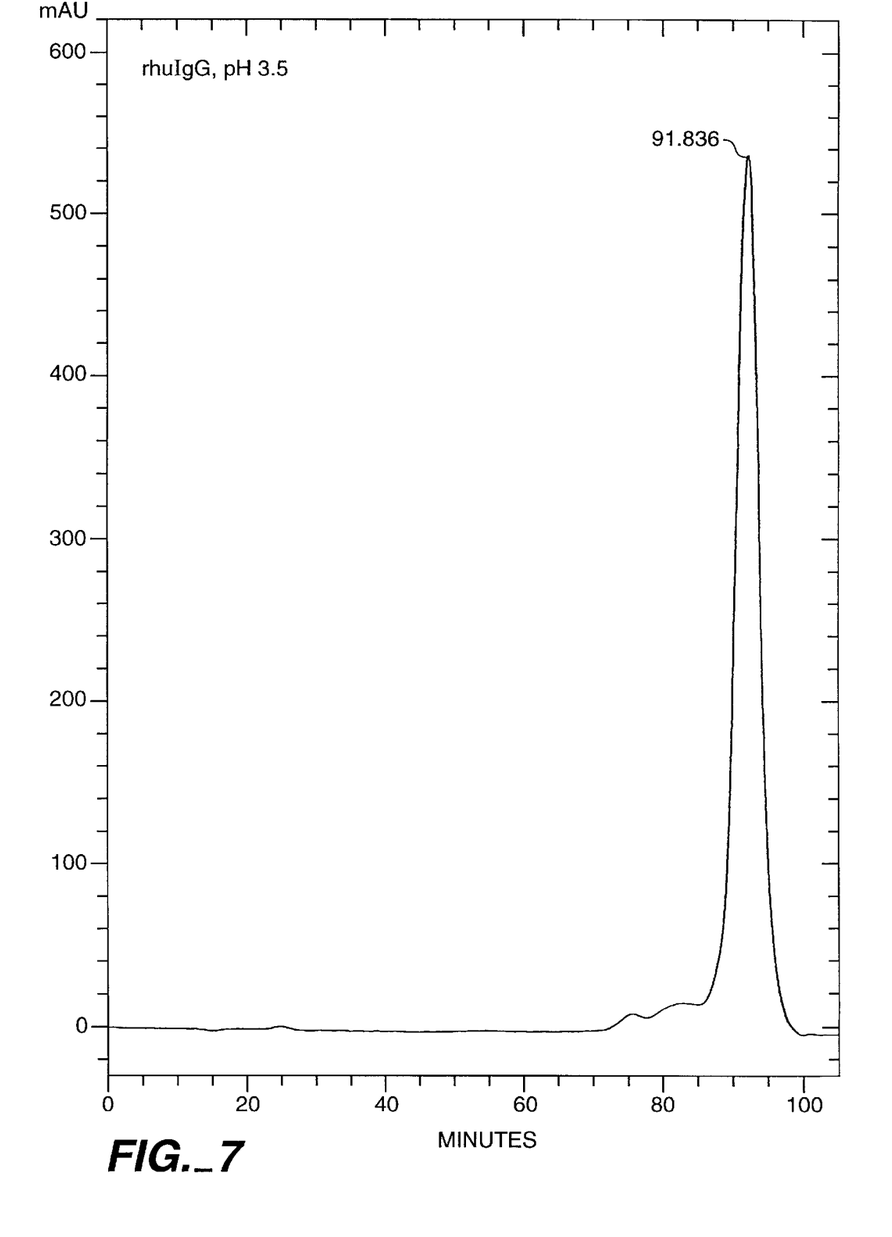
FIG. 7 shows the elution profile of rhulgG off of a Superose 6 size exclusion chromatography column. The rhulgG protein was loaded onto the column at a concentration of 0.8 mg/ml in a buffer of 0.1 M acetic acid, 0.15 M NaCl, pH 3.5±0.1 and with a load volume of 0.2%. Data is plotted as UV absorbance units (mAU) versus time in minutes (min).
Figure 8:
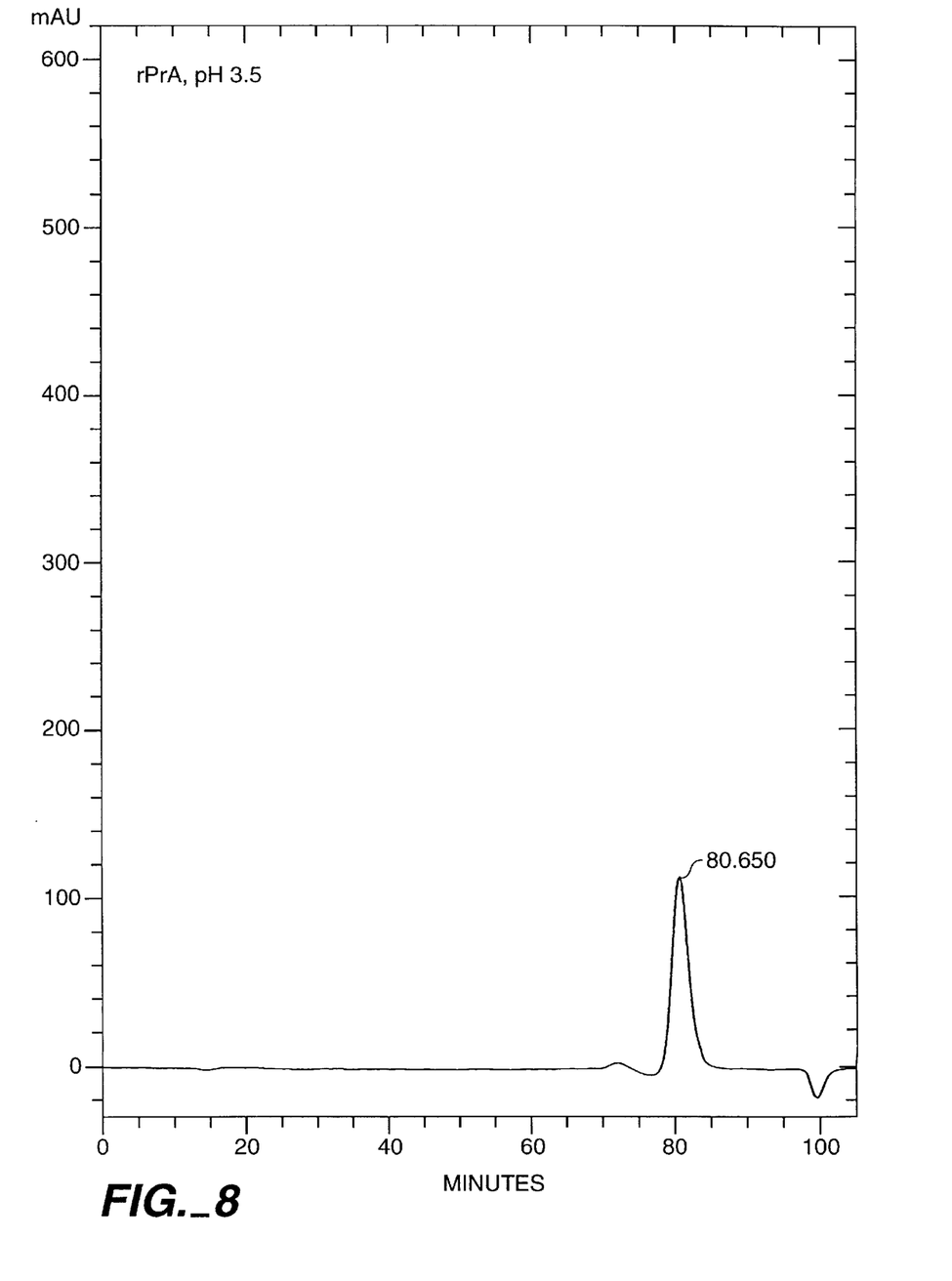
FIG. 8 shows the elution profile of rPrA off of a Superose 6 size exclusion chromatography column. The rPrA protein was loaded onto the column at a concentration of 0.2 mg/ml in a buffer of 0.1 M acetic acid, 0.15 M NaCl, pH 3.5±0.1 and with a load volume of 0.2%. Data is plotted as UV absorbance units (mAU) versus time in minutes (min).

Under the new, more acidic buffer conditions, analysis of the: individual samples of rhuIgG and rPrA showed retention times of 91.8 minutes for rhuIgG (FIG. 7) and 80.6 minutes for rPrA (FIG. 8).

Figure 9:
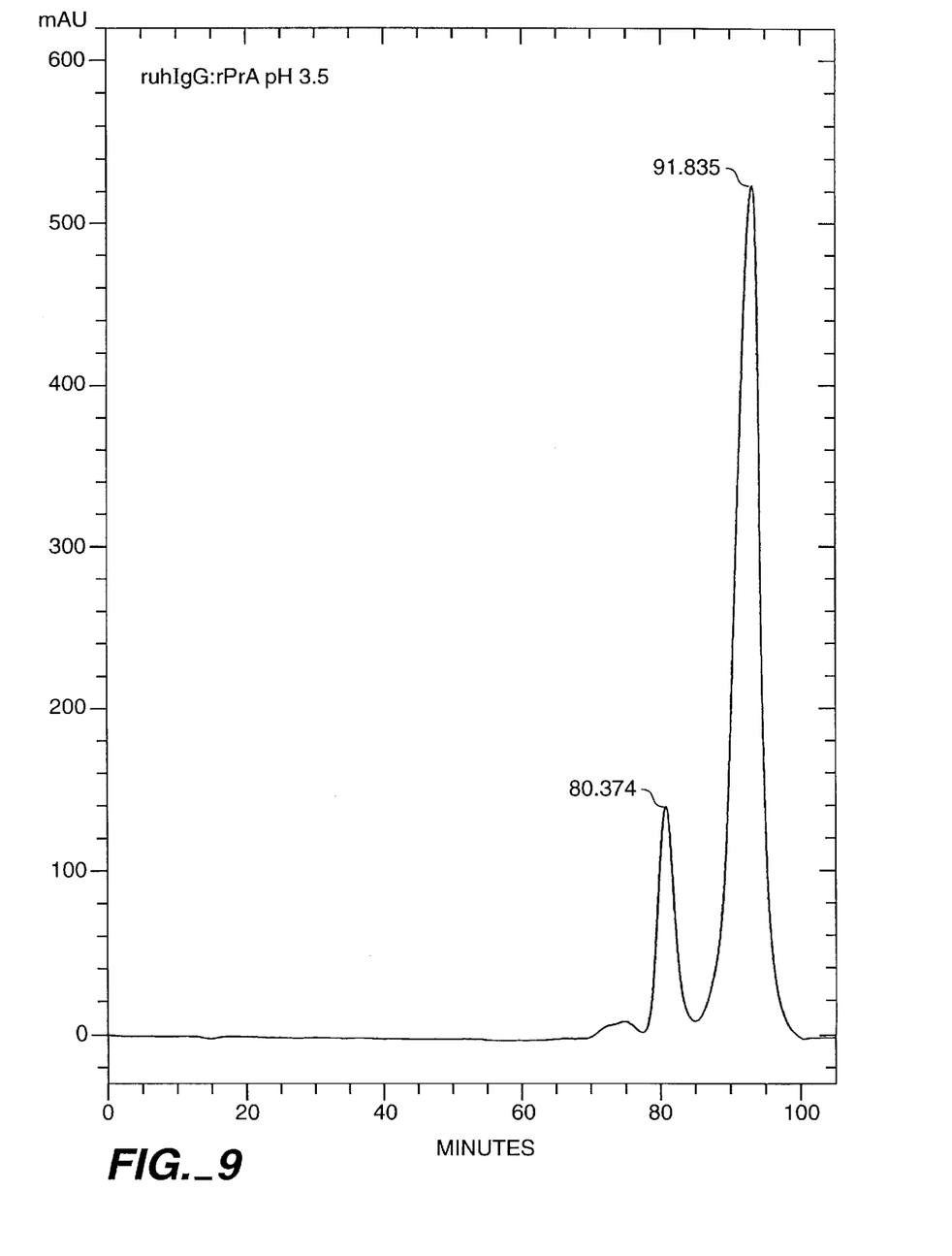
FIG. 9 shows the elution profile of a rhulgG/rPrA off of a Superose 6 size exclusion chromatography column. The rhulgG and rPrA proteins were loaded onto the column at a concentration of 0.8 mg/ml and 0.2 mg/ml, respectively, in a buffer of 0.1 M acetic acid, 0.15 M NaCl, pH 3.5±0.1 and with a load volume of 0.2%. Data is plotted as UV absorbance units (mAU) versus time in minutes (min).

Analysis of an injection of the complex showed baseline separation of two peaks with retention times corresponding to the peaks for the individual rhuIgG and rPrA components (FIG. 9; 91.8 minutes and 80.4 minutes, respectively). These results indicate that the complex is separating into the individual rhuIgG and rPrA components under these conditions so that the rhuIgG pool can be collected as a purified product.

The results presented above demonstrate that the separation of an impurity from a protein product can be achieved in free solution by the addition of a lower molecular weight ligand which is capable of interacting with the protein product, thereby altering the molecular weight and hydrodynamic volume of the protein product and rendering it separable from the impurity. As demonstrated above, affinity binding allowed the formation of the protein/ligand complex rhuIgG/rPrA. This interaction altered the properties of the protein rhuIgG, thereby forming a molecule with a larger hydrodynamic volume. These new properties allowed separation of the BSA impurity from the rhuIgG protein using HPLC-SEC. After separation of the complex from the impurity, the complex was then successfully dissociated into its individual components by altering the solution conditions, pH and ionic strength. Final purification of the rhuIgG product was achieved by separation of the individual protein and ligand molecules using HPLC-SEC.

The foregoing description details specific methods which can be employed to practice the present invention. Having detailed such specific methods, those skilled in the art will well enough know how to devise alternative reliable methods at arriving at the same information in using the fruits of the present invention. Thus, however, detailed the foregoing may appear in text, it should not be construed as limiting the overall scope thereof; rather, the ambient of the present invention is to be determined only by the lawful construction of the appended claims. All documents cited herein are expressly incorporated by reference.

What is claimed is:

1. A method for separating a first species from a second species in a free solution mixture comprising said first and second species, said first and second species have about the same hydrodynamic volume, said method comprising:

contacting said free solution mixture with a ligand soluble in said free solution mixture, wherein said ligand interacts with said first species, wherein the molecular weight of said ligand is smaller than the molecular weight of said first species and wherein said interaction forms a first species/ligand complex which complex has a different hydrodynamic volume from said second species in free solution; and separating said first species/ligand complex from said second species, by size exclusion chromatography, and wherein the first species is a polypeptide.

2. The method according to claim 1, wherein said first species of interest is an antibody.

3. The method according to claim 1, wherein said polypeptide is recombinantly produced.

4. The method according to claim 1, wherein said polypeptide comprises an immunogammaglobulin moiety and wherein said ligand is Protein A.

5. The method according to claim 1, wherein said step of separating is accomplished by size exclusion chromatography.

6. The method according to claim 5, wherein said size exclusion chromatography is performed at an ionic strength of less than about 100 mM.

7. The method according to claim 1 further comprising the step of dissociating said first species ligand complex into its individual components, wherein dissociating occurs after said step of separating.

8. The method according to claim 1, wherein said ligand does not interact with said second species.

9. The method according to claim 1, wherein said second species is an impurity.

* * * * *